(12) United States Patent
Kiefer

(10) Patent No.: US 9,750,665 B2
(45) Date of Patent: Sep. 5, 2017

(54) FEEDING TUBE APERTURE

(71) Applicant: Henry Kiefer, Casper, WY (US)

(72) Inventor: Henry Kiefer, Casper, WY (US)

(*) Notice: Subject to any disclaimer, the term of this patent is extended or adjusted under 35 U.S.C. 154(b) by 119 days.

(21) Appl. No.: 15/053,386

(22) Filed: Feb. 25, 2016

(65) Prior Publication Data

US 2016/0199263 A1    Jul. 14, 2016

Related U.S. Application Data

(63) Continuation-in-part of application No. 13/253,945, filed on Oct. 5, 2011, now abandoned.

(51) Int. Cl.
*A61J 15/00* (2006.01)
*A61M 39/02* (2006.01)
*A61M 39/12* (2006.01)
*A61M 25/02* (2006.01)
*A61M 39/10* (2006.01)

(52) U.S. Cl.
CPC ....... *A61J 15/0061* (2013.01); *A61J 15/0015* (2013.01); *A61J 15/0034* (2013.01); *A61J 15/0096* (2013.01); *A61M 39/0247* (2013.01); *A61M 39/105* (2013.01); *A61M 39/12* (2013.01); *A61M 2025/0233* (2013.01); *A61M 2039/0255* (2013.01); *A61M 2039/0261* (2013.01); *A61M 2039/0264* (2013.01); *A61M 2039/0276* (2013.01); *A61M 2039/0282* (2013.01); *A61M 2039/0285* (2013.01); *A61M 2039/0288* (2013.01); *A61M 2039/1066* (2013.01)

(58) Field of Classification Search
CPC ................ A61J 15/0015; A61J 15/0061; A61J 15/0096; A61J 15/0034; A61M 2025/0233; A61M 2039/0255; A61M 2039/0282; A61M 2039/0261; A61M 2039/0264; A61M 2039/0276
See application file for complete search history.

(56) References Cited

U.S. PATENT DOCUMENTS 4,344,435 A * 8/1982 Aubin ................. A61J 15/0015
                                                              604/246
4,393,873 A    7/1983 Nawash et al.
4,397,647 A    8/1983 Gordon
(Continued)

*Primary Examiner* — Emily Schmidt
*Assistant Examiner* — Shefali Patel
(74) *Attorney, Agent, or Firm* — Davis & Bujold PLLC; Michael J. Bujold

(57) ABSTRACT

A feeding tube aperture supported and aligned with a feeding tube opening in an abdominal wall of a patient, including a base having a first end surface transverse to an axis of the base and a feeding tube, a second opposed end surface, a central feeding tube passage extending between the first and second end surfaces, a plurality of vent passages around the feeding tube passage and extending between the first and second end surfaces, a hollow, cylindrical feeding tube support extension centered on and extending outwardly from the feeding tube passage to support and align the feeding tube aperture, and a plurality of spaced apart resilient spacers extending outwards from the second end surface. The plurality of spaced apart resilient spacers resiliently space the second end surface from the abdominal wall and form a plurality of air passages to allow a flow of air around the abdominal wall and the feeding tube opening.

3 Claims, 3 Drawing Sheets

(56) References Cited

U.S. PATENT DOCUMENTS

| | | | |
|---|---|---|---|
| 4,666,433 A * | 5/1987 | Parks | A61J 15/0015 128/DIG. 12 |
| 5,792,119 A | 8/1998 | Marx | |
| 7,410,477 B2 * | 8/2008 | Gomez | A61M 25/02 604/96.01 |
| 2011/0288534 A1 | 11/2011 | Aguirre et al. | |

* cited by examiner

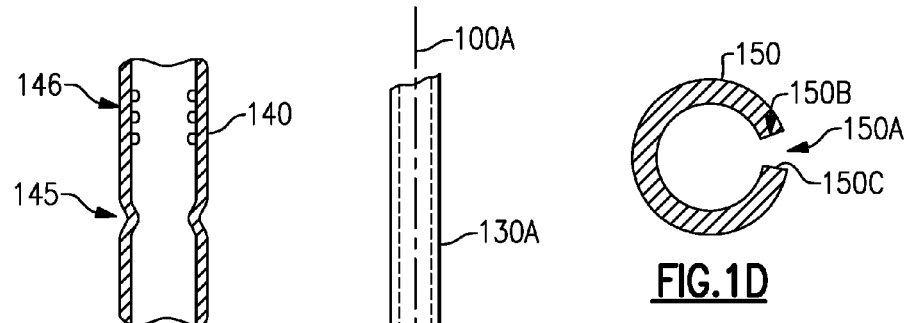
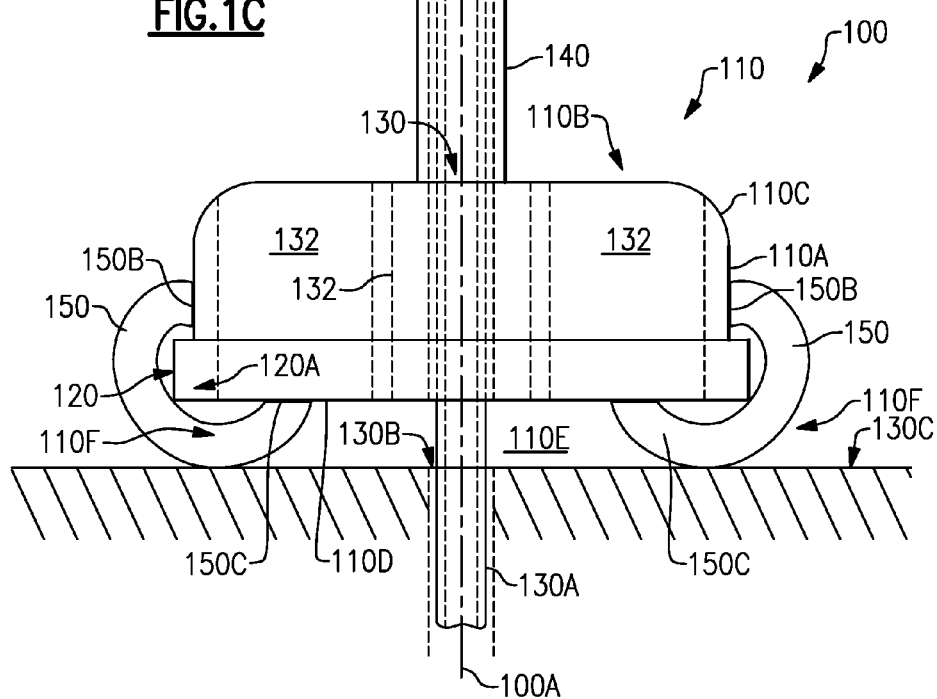

FEEDING TUBE APERTURE

CROSS REFERENCES TO RELATED APPLICATIONS

The present Application is related to and claims benefit of U.S. patent application Ser. No. 13/253,945 for a Feeding Tube Aperture filed Oct. 5, 2011 by Henry Kiefer.

FIELD OF THE INVENTION

The present invention relates to the gavage administration of liquid foods and medications directly to the stomach of a patient through a feeding tube extending from the interior of the patient's stomach and through, for example, the patient's abdominal wall, to an exterior source of liquid food or medication or both and, in particular to a feeding tube aperture positioned generally at exterior of the patient's abdominal wall to support the feeding tube.

BACKGROUND OF THE INVENTION

Many medical processes, such as treatment for cancer in a patient's thoracic region, require the long term implantation of a gavage feeding tube, hereafter generally referred to as a "feeding tube," that is anchored in the patient's stomach and extends through the patient's abdominal wall and skin to an exterior source of liquid food or medications. The implantation of such feeding tubes, however, often results in further medical problems for a number of reasons, such as movement of the stomach itself or relative movement between the patient and the exterior source of liquid food or medication, which often result in displacement of the feeding tube and frequently results in laceration, puncturing, distortion or irritation of the feeding tube opening through the abdominal wall. It is therefore generally necessary to provide some means of feeding tube support at the feeding tube opening to prevent or limit motion between the feeding tube and the abdominal wall and skin of the patient in this region.

Feeding tube support devices of the prior art have proven generally unsatisfactory for general use for a number of reasons. For example, the devices described in U.S. Pat. No. 5,792,119 to Marx for a TUBULAR IMPLANT TO BE USED FOR PERCUTANEOUSLY FEED A PATIENT, U.S. Pat. No. 4,344,435 to Aubin for a METHOD AND SURGICALLY IMPLANTABLE APPARATUS FOR PROVIDING FLUID COMMUNICATION WITH THE INTERIOR OF THE BODY, U.S. Patent Application Publication No. US2011/0288534 to Aguirre et al. For a DEVICE FOR EXTERNAL PERCUTANEOUS CONNECTIONS, and U.S. Pat. No. 4,393,873 to Nawash et al. For a GASTROSTOMY AND OTHER PERCUTANEOUS TUBES are generally too complex in structure, or require complex implantation methods and apparatus, and therefore too expensive for general use.

In addition, such devices are often and typically detrimental to the patient. For example, the feeding tube support devices of the prior art generally entrap body fluids seeping from the patient's body in the region around the opening through which the feeding tube penetrates the patient's skin while preventing or limiting the flow of air to and cleaning access to the region around the feeding tube opening. These limitations generally result in irritation to and very possibly necrosis of the patent's skin in the region around the feeding tube, and possibly even within the feeding tube passage through the patient's abdominal wall. In addition, the feeding tube support devices of the prior art are typically rigid structures of significant size and frequently cause discomfort to the patient by digging into the skin of the patient as the patient moves about.

Certain other feeding tube devices of the prior art, such as that described in U.S. Pat. No. 4,397,647 to Gordon for a CATHETER STABLIZATION FITTING HAVING A SNAP-OVER COVER, may provide some support to a feeding tube but are attached to the patient at some distance from the feeding tube opening through the patient's abdominal wall and mere prevent or limit disturbance to the feeding tube due to movement between the patient and the exterior source of liquid food or medication and do not and cannot provide the necessary support in the region of the feeding tube opening through the patient's abdominal wall.

Other feeding tube support devices of the prior art, such as that described in U.S. Pat. No. 4,666,433 to Parks for a GASTROSTOMY FEEDING DEVICE, have the virtue of simplicity and thus of reasonable cost, but also have the limitations and disadvantages of the above discussed devices of the prior art. For example, the Parks '433 device includes a disk-like element that bears against the skin of the patient in the region around the feeding tube opening, this providing at least some degree of discomfort to the patient as discussed above. While Parks '433 purports to provide openings through the disk-like element that bears against the skin of the patient around feeding tube opening for to provide air circulation, it is apparent that the described openings are too small to provide any useful degree of air circulation and are in any case blocked by the skin of the patient. The Parks '433 embodiment having radial ridges on the bottom of the disk-like element to space the disk-like element from the skin of the patient still only allows very limited air circulation as the ridges themselves limit air circulation; in addition, the hard, sharp edged ridges will themselves be yet another source of irritation to the skin around the feeding tube opening.

It is therefore apparent that the prior art does not offer a feeding tube support device that offers medical patients comfortable, easy-to-use support for feeding tubes or a feeding tube support device that will not puncture, rip or otherwise irritate the skin around a feeding tube opening or the internal tissue lining of a feeding tube passage or that can reliably prevent necrosis and possible infection.

BRIEF DESCRIPTION OF THE DRAWINGS

The present invention will be described by way of exemplary embodiments, but not limitations, illustrated in the accompanying drawings in which like references denote similar elements, and in which:

FIG. 1B shows a side view of a feeding tube aperture;

FIG. 1C shows a sectional side view of a feeding tube support extension;

FIG. 1D shows a sectional end view of a resilient spacer; and

SUMMARY OF THE INVENTION

Figure 1A:
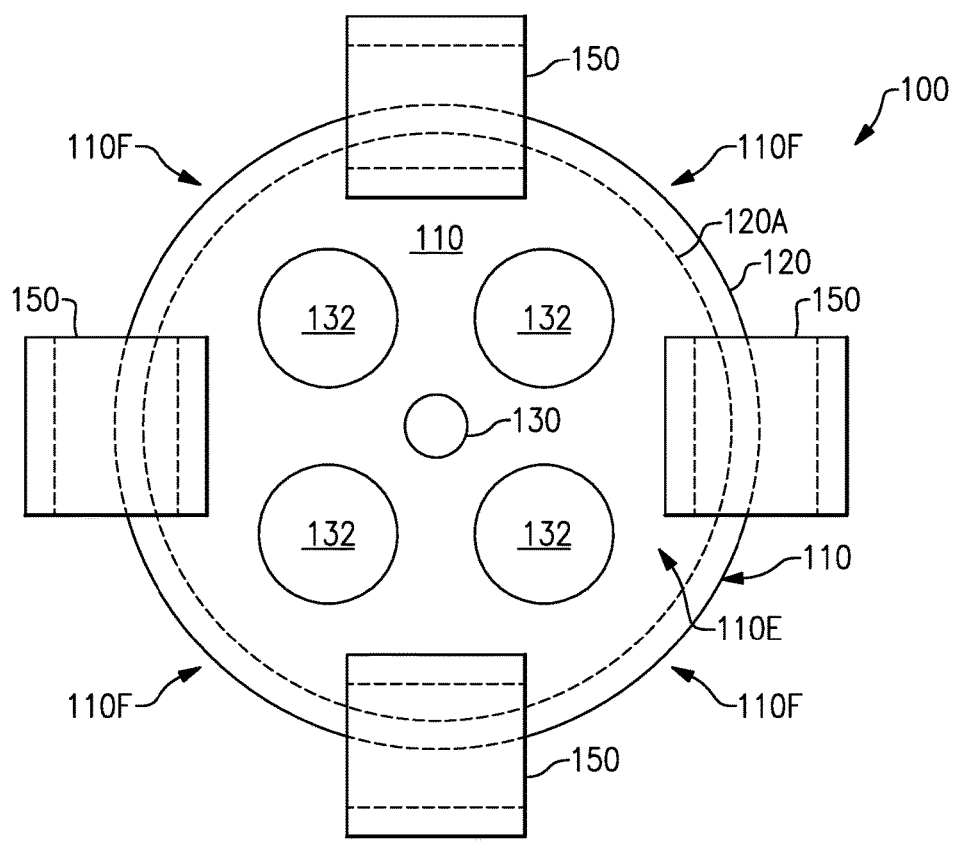
FIG. 1A shows an end view of a feeding tube aperture.

A feeding tube aperture positionable at an external abdominal wall of a patient and along a feeding tube extending through the abdominal wall of the patient to support and align the feeding tube with a feeding tube opening through the abdominal wall of the patient.

In a present embodiment the feeding tube aperture includes a base having a circumferential surface symmetric about an axis, a first end surface transverse to the axis, a second end surface transverse to the axis and facing in an axially opposite direction from the first end surface, a centrally located feeding tube passage extending along the axis and through the base from the first end surface to the second end surface and having an interior diameter accommodating the feeding tube in a slidable frictional engagement between the feeding tube and an interior surface of feeding tube passage, a hollow, cylindrical feeding tube support extension extending outwardly from the first end surface and axially centered on the axis with an interior diameter accommodating the feeding tube in a slidable frictional engagement between the feeding tube and an interior surface of the feeding tube support extension, a plurality of large axial vent passages occupying a region between the centrally located feeding tube passage and the circumferential surface and extending through the base from the first end surface to the second end surface with the axial vent passages being disposed symmetrically around the centrally located feeding tube passage, and a plurality of resilient spacers extending outwards from the second end surface and spaced circumferentially apart around a circumference of the second end surface.

When the feeding tube aperture is mounted onto a feeding tube with the second end surface oriented toward and directly adjacent the abdominal wall with the resilient spacers in contact with the abdominal wall the feeding tube aperture is resiliently spaced apart from the abdominal wall by the resilient spacers, and the resilient spacers form an air space between the second end surface and the abdominal wall and a plurality of circumferential vent passages between the air space and the resilient spacers, so that the axial vent passages through the base, the air space between the second end surface and the abdominal wall and the circumferential vent passages allow a flow of air around the abdominal wall and the feeding tube opening in the abdominal wall.

In further embodiments of the feeding tube aperture, the feeding tube aperture may include a circumferential flange located on the circumference of the second end surface and extending outwards from second end surface, and each of the resilient spacers is comprised of a generally cylindrical hollow tube of resilient foam with a longitudinal opening extending lengthwise from end to end along a wall of the resilient spacer wherein each resilient spacer is attached to the feeding tube aperture by mounting the resilient spacer at a selected location on the circumference of the circumferential flange with one side of the longitudinal opening of the longitudinal opening bearing against the base in the region of the circumferential surface of the base an adjacent surface of the circumferential flange and a second side of the longitudinal opening bearing against an inner edge of circumferential flange and second end surface.

In still further embodiments, the interior surface of the feeding tube support extension may further include at least one of at least one crimped region and at least one raised nub to engage the feeding tube to resist inadvertent movement between the feeding tube and the feeding tube aperture.

DETAILED DESCRIPTION OF ILLUSTRATIVE EMBODIMENTS

Figure 2:
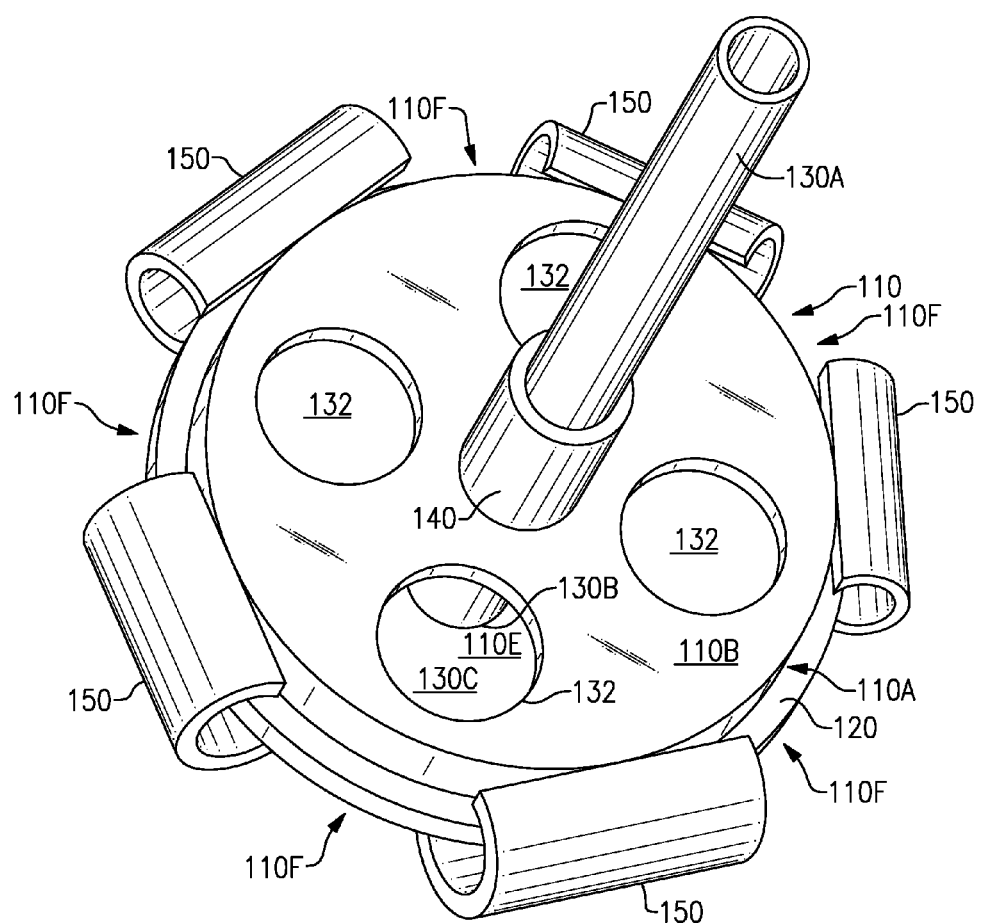
FIG. 2 is an isometric view of a feeding tube aperture.

A feeding tube aperture of the present invention will be described in the following with reference to FIGS. 1A, 1B, 1C and 1D and FIG. 2 wherein FIGS. 1A and 1B are respectively diagrammatic illustrations of an end view and a sectional side view of a feeding tube aperture 100 of the present invention. FIG. 1C is a side cross section view of a part of a feeding tube support extension, FIG. 1D is an end cross section view of a resilient spacer and FIG. 2 is an isometric diagrammatic view of a feeding tube aperture 100 of the present invention.

As illustrated therein, a feeding tube aperture 100 is generally disk shaped and includes a base 110 having a circumferential surface 110A symmetric about an axis 100A, a first end surface 116E transverse to axis 100A with a circumferential curved surface 110C extending between and joining circumferential surface 110A and first end surface 110B, a second end surface 110D transverse to axis 100A and facing in an axially opposite direction from first end surface 110B, and may include a circumferential flange 120 located on the circumference 120A of second end surface 110D.

Feeding tube aperture 100 includes a centrally located feeding tube passage 130 extending along axis 100A and through base 110 from first end surface 110E to second end surface 110D. The interior diameter of feeding tube passage 130 has a diameter to accommodate a feeding tube 130A in a slidable friction engagement between a feeding tube 130A and the interior surface of feeding tube passage 130. In use, feeding tube aperture 100 will be oriented with first end surface 110A facing away from an abdominal wall 130C of a patient and second end surface 110B facing toward the abdominal wall 130C with a feeding tube 130A extending from a feeding tube opening 130B in the abdominal wall 130C of a patient and passing through feeding tube passage 130 so that the feeding tube 130A and will be secured by feeding tube aperture 100 in a generally perpendicular orientation to the abdominal wall 130C of the patient.

Feeding tube aperture 100 further includes a plurality of relatively large axial vent passages 132 occupying the region between central feeding tube passage 130 and circumferential surface 110A of base 110 and extending through base 110 from first end surface 110B to second end surface 110D with axial vent passages 132 generally being disposed symmetrically around feeding tube passage 130. It will also be noted that axial vent passages 132 together occupy a relatively large portion of the areas of first end surface 110B and second end surface 110D, as illustrated in FIGS. 1A, 1B and 2 and as will be discussed further below.

In a presently preferred embodiment, a feeding tube aperture 100 further includes a hollow, cylindrical feeding tube support extension 140 that is secured to and extends outwardly from first end surface 110B with feeding tube support extension 140 being axially centered on axis 100A and feeding tube passage 130. Feeding tube support extension 140 has an interior diameter accommodating a feeding tube 130A to allow a feeding tube 130A to pass through feeding tube support extension 140 in a slidable friction engagement between a feeding tube 130A and the interior surface of feeding tube passage 130. For these purposes, and as illustrated in FIG. 10, feeding tube support extension 140 may include crimped regions 145 or a plurality of internal raised nubs 146 disposed on the interior surface 144 of feeding tube support extension 140 to prevent the plastic tube anchor 140 from inadvertently sliding or supping along the feeding tube 130A. Lastly, feeding tube support extension 140 may, for example, be a separate element that is secured to base 110, for example by glue or a mechanical joint, or may be cast or molded as an integral part of base 110 and circumferential flange 120.

A feeding tube aperture 100 further includes a plurality of resilient foam "booties," hereafter referred to as resilient spacers 150, mounted to and spaced circumferentially apart from each other around the circumference 120A of second end surface 11 OD with resilient spacers 150 extending outwards from the second end surface 11 OD. It will be noted that the number of resilient spacers 150 may vary, depending on the specific embodiment of a feeding tube aperture 100, but there will typically be at least three resilient spacers and may be four, as illustrated in FIG. 1B, or five, as illustrated in FIG. 2. It must also be noted that for purposes of clarity showing other elements of a feeding tube aperture 100, only two opposed mounted resilient spacers 150 are illustrated in FIG. 1A; it will be understood, however, that as stated and as shown in FIGS. 1B and 2, a feeding tube aperture 100 will include 3 or more resilient spacers 150, such as four or five or more.

When feeding tube aperture 100 is in use, as illustrated in FIGS. 1A, 1B and 2, the feeding tube aperture 100 is slidingly mounted onto a feeding tube 130A and directly adjacent to the patient's abdominal wall 130C with feeding tube aperture 100 oriented with first end surface 110B and feeding tube support extension 140 facing away from abdominal wall 130C of a patient and second end surface 110D facing toward abdominal wall 130C with a feeding tube 130A extending from a feeding tube opening 130B in the abdominal wall 130C. Resilient spacers 150 will then bear against abdominal wall 130C so that second end surface 110D will thereby be resiliently spaced apart from abdominal wall 130C.

Because resilient spacers 150 are located around the circumference 120A of second end surface 110D, resilient spacers 150 are thereby radially spaced apart from the feeding tube opening 130B in the abdominal wall 130C of a patient. Feeding tube aperture 100 therefore does not exert pressure directly on feeding tube opening 130B or the area immediately surrounding feeding tube opening 130B and such pressure as is exerted against abdominal wall 130C by feeding tube aperture 100 is resiliently cushioned and distributed over a signification area of the surrounding abdominal wall 130C by resilient spacers 150.

As further illustrated in FIGS. 1A, 1B and 3, resilient spacers 150 occupy only a portion of the circumference 120A of second end surface 110D, being illustrated in the figures as approximately half or less of the circumference 120A of second end surface 110C. The circumferential spacing of resilient spacers 150 around the circumference 120A of second end surface 110D, together with second end surface 110D of feeding tube aperture 100 being spaced apart from abdominal wall 130C and feeding tube opening 130B by resilient spacers 150, thereby provides a relatively large air space 110E between second end surface 110D and abdominal wall 130C and a plurality of relatively large circumferential vent passages 110F between air space 110E and the exterior surroundings of the feeding tube aperture 100. Axial vent passages 132 through base 110, air space 110E between second end surface 110D and circumferential vent passages 110F thereby provide significantly increased air flow to and around the area between abdominal wall 130C and feeding tube opening 130B and feeding tube aperture 100, thereby significantly reducing the risk of irritation, infection and necrosis of the tissues at or around feeding tube opening 130B.

In a present embodiment of a feeding tube aperture 100, and as illustrated in FIGS. 1A, 1B, 1D and 2, each resilient spacer 150 comprises a generally cylindrical hollow tube of resilient foam with a longitudinal opening 150A extending lengthwise from end to end along the wall 150B of the resilient spacer 150. Resilient spacers 150 are attached to feeding tube aperture 100 by mounting each resilient spacer 150 at a selected location on circumferential flange 120 with circumferential flange 120 entering into longitudinal opening 150A. As indicated, a first side 150E of longitudinal opening 150A will thereby bear against base 110 in the region of circumferential surface 110A and the adjoining area of circumferential flange 120 and a second side 150C side of longitudinal opening 150A will bear against second end surface 110D of base 110. The resilience of the foam material comprising resilient spacers 150 will retain resilient spacers 150 on feeding tube aperture 100 and circumferential flange 120, but resilient spacers 150 may be further secured to feeding tube aperture by, for example, an adhesive or glue. It will also be noted that the resilient of the foam material comprising resilient spacers 150 will tend to allow resilient spacers 150 to conform to the curvature of circumferential flange 120, but resilient spacers 150 may be molded with a curvature matching that of circumferential flange 120 or circumference 120A of second end surface 110D.

It will be further understood that resilient spacers 150 may assume other forms, such as blocks or legs of resilient foam secured to second end surface 110D or to second end surface 110G and circumferential flange 120, such as by adhesives or glue, so long as such resilient spacers 150 occupy only a portion of the circumference 120A of second end surface 110D and resiliently space second end surface 110D and feeding tube aperture 100 apart from abdominal wall 130C to provide relatively large air spaces and air passages between second end surface 110D and abdominal wall 130C with feeding tube opening 130B to thereby provide significantly increased air flow to and around the area between abdominal wall 130C and feeding tube opening 130B and feeding tube aperture 100. Further in this regard, it will be recognized that in the present shown exemplary embodiment of a feeding tube aperture 100 of the present invention the primary function of circumferential flange 120 is to provide a means for attaching the illustrated resilient spacers 150 to the feeding tube aperture 100, and that certain alternative implementations of resilient spacers 150 may not require a circumferential flange 120.

Lastly with regard to use of a feeding tube aperture 100 of the present invention, it has been described above that the interior diameters and configurations of feeding tube passage 130 and feeding tube support extension 140 are selected to engage a feeding tube 130A in a sliding frictional engagement so that the feeding tube aperture 100 will not slide inadvertently with respect to the feeding tube 130A. At the same time, the interior diameters and configurations of feeding tube passage 130 and feeding tube support extension 140 are selected to allow the feeding tube aperture 100 to be intentionally slide along the feeding tube 130A to allow the feeding tube aperture 100 to be moved away from abdominal wall 130C and feeding tube opening 130B to allow cleaning of the feeding tube aperture 100, abdominal wall 130C and feeding tube opening 130B, and any medical treatment that may be necessary or desirable.

In a present embodiment of a feeding tube aperture 100, the axial length of feeding tube aperture 100, that is of base 110 and circumferential flange 120, is on the order of 0.75 inches and the diameter of circumferential flange 120 is on the order of 2.00 inches and feeding tube aperture 100 includes four symmetrically disposed circular axial vent passages 132 having diameters on the order of 0.5 inches while the diameter of feeding tube passage 130 and thus the interior diameter of feeding tube support extension 140 are selected to provide a frictional sliding fit with a feeding tube 130A, typically about 0.25 inches. It will be understood, however, that these dimensions may differ from those illustrated in the exemplary present embodiment of a feeding tube aperture 100, depending upon the specific application and use and the diameter of the feeding tubes 130A with which the feeding tube aperture 100 is to be used.

Lastly, in the present exemplary embodiment of a feeding tube aperture 100 and feeding tube support extension 140 the feeding tube aperture 100 and feeding tube support extension 140 will typically be cast or molded from a plastic material and feeding tube aperture 100 and feeding tube support extension 140 may comprise separate pieces joined mechanically or by an adhesive or glue or may be cast or molded as a single, integral body. The material comprising feeding tube aperture 100 and feeding tube support extension 140 will preferably accommodate various sterilization processes and will preferably have smooth surfaces to reduce accumulated deposits of body fluids, liquid food or medication, to facilitate cleaning of the feeding tube aperture 100, feeding tube opening 130B and the abdominal wall 130C around feeding tube aperture 130, and to reduce potential irritation to the patient.

While the present invention has been related in terms of the foregoing embodiments, those skilled in the art will recognize that the invention is not limited to the embodiments described. The present invention can be practiced with modification and alteration within the spirit and scope of the appended claims. Thus, the description is to be regarded as illustrative instead of restrictive on the present invention.

What is claimed is:

1. A feeding tube aperture positionable at an external abdominal wall of a patient and along a feeding tube extending through the abdominal wall of the patient to support and align the feeding tube with a feeding tube opening through the abdominal wall of the patient, comprising:
    a base having
        a circumferential surface symmetric about an axis,
        a first end surface transverse to the axis,
        a second end surface transverse to the axis and facing in an axially opposite direction from the first end surface,
        a centrally located feeding tube passage extending along the axis and through the base from the first end surface to the second end surface and having an interior diameter accommodating the feeding tube in a slidable frictional engagement between the feeding tube and an interior surface of the feeding tube passage,
        a plurality of large axial vent passages occupying a region between the centrally located feeding tube passage and the circumferential surface and extending through the base from the first end surface to the second end surface with the plurality of large axial vent passages being disposed symmetrically around the centrally located feeding tube passage,
    a hollow, cylindrical feeding tube support extension extending outwardly from the first end surface and axially centered on the axis with an interior diameter accommodating the feeding tube in a slidable frictional engagement between the feeding tube and an interior surface of the feeding tube support extension, and
    a plurality of resilient spacers attached to a circumference of the second end surface and extending outward from the second end surface, the plurality of resilient spacers being spaced circumferentially apart around the circumference of the second end surface with a longitudinal axis of each of the plurality of resilient spacers extending generally along the circumference of the second end surface, so that
        when the feeding tube aperture is mounted onto the feeding tube with the second end surface oriented toward and directly adjacent the abdominal wall with the plurality of resilient spacers in contact with the abdominal wall,
            the feeding tube aperture is resiliently spaced from the abdominal wall by the plurality of resilient spacers, and
            the plurality of resilient spacers form a common air space located between the second end surface and the abdominal wall, the air space extending from the centrally located feeding tube passage to the circumference of the second end surface and communicating with each of the plurality of large axial vent passages and with each of a plurality of circumferential vent passages formed between adjacent pairs of the plurality of resilient spacers, so that the plurality of large axial vent passages through the base, the air space between the second end surface and the abdominal wall and the plurality of circumferential vent passages allow a flow of air around the abdominal wall and the feeding tube opening in the abdominal wall during use.

2. The feeding tube aperture of claim 1, further comprising:
    a circumferential flange located on the circumference of the second end surface and extending outwards from the second end surface, wherein
    each of the plurality of resilient spacers comprises a generally cylindrical hollow tube of resilient foam with a longitudinal opening in a wall of the generally cylindrical hollow tube extending lengthwise along the longitudinal axis of each of the plurality of resilient spacers, and
    each of the plurality of resilient spacers is attached to the feeding tube aperture by mounting each of the resilient spacers at a selected location on a circumference of the circumferential flange with a first side of the longitudinal opening bearing against the base in a region of the circumferential surface of the base and an adjoining surface of the circumferential flange and a second side of the longitudinal opening bearing against the second end surface of the base.

3. The feeding tube aperture of claim 1, further comprising:
    a circumferential flange located on the circumference of the second end surface and extending outwards from the second end surface, wherein
    each of the plurality of resilient spacers comprises a generally cylindrical hollow tube of resilient foam having a longitudinal opening formed in a wall of the generally cylindrical hollow tube, and
    each of the plurality of resilient spacers is attached to the feeding tube aperture via engagement of the longitudinal opening with the circumference of the second end surface.

* * * * *